United States Patent
Levorse, Jr. et al.

(10) Patent No.: US 9,701,925 B2
(45) Date of Patent: Jul. 11, 2017

(54) CYCLOPENTANOL COMPOUNDS

(71) Applicant: INTERNATIONAL FLAVORS & FRAGRANCES INC., New York, NY (US)

(72) Inventors: Anthony Levorse, Jr., Westfield, NJ (US); Nicole Giffin, Hazlet, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 56 days.

(21) Appl. No.: 15/041,456

(22) Filed: Feb. 11, 2016

(65) Prior Publication Data

US 2016/0160152 A1  Jun. 9, 2016

Related U.S. Application Data

(62) Division of application No. 14/103,100, filed on Dec. 11, 2013, now Pat. No. 9,290,718.

(51) Int. Cl.
*C11B 9/00* (2006.01)
*C07C 35/06* (2006.01)
*C07C 35/21* (2006.01)

(52) U.S. Cl.
CPC .............. *C11B 9/003* (2013.01); *C07C 35/06* (2013.01); *C07C 35/21* (2013.01)

(58) Field of Classification Search
CPC ........... A61Q 13/00; A61K 8/00; C07C 13/10
USPC ............................................................ 512/8
See application file for complete search history.

(56) References Cited

U.S. PATENT DOCUMENTS 3,769,330 A * 10/1973 Nikawitz ................. C07C 1/24
                                                            512/23

* cited by examiner

*Primary Examiner* — Lanee Reuther
(74) *Attorney, Agent, or Firm* — Martin Zhang; XuFan Tseng; Elizabeth M. Stover

(57) ABSTRACT

The present invention pertains to novel cyclopentanols and their unexpected advantageous use thereof in enhancing, improving or modifying the fragrance of perfumes, colognes, toilet waters, fabric care products, personal products, and the like.

7 Claims, No Drawings

CYCLOPENTANOL COMPOUNDS

STATUS OF RELATED APPLICATIONS

This application is a divisional of U.S. Ser. No. 14/103,100, filed Dec. 11, 2013, now allowed, the content hereby incorporated by reference as if set forth in its entirety.

FIELD OF THE INVENTION

The present invention relates to novel chemical entities and a method of using the same as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances. For example, benzene compounds that differ slightly in substituents possess completely different odor profiles [Ishikawa, et al., International Journal of Quantum Chemistry 79: 101-108 (2000)]. In the case of tert-butyl cyclohexanes, the odor is said to be dependent on the compounds' conformation and therefore analogs adopting same conformation possess similar odor. Accordingly, many trans-compounds are shown to share pronounced urine-perspiration-type odor, while the corresponding cis-compounds are odorless or at the most possess weak and undefinable flowery or woody odor. However, some other trans- and cis-tert-butyl cyclohexanes are shown to possess opposite sensory activities [Ohloff, et al., Helvetica Chimica Acta 66, Fasc. 5: 1343-1354 (1983)]. Thus, it is hard for those with skill in the art to predict a given structure would be effective in sensory activities. Identifying desirable fragrance chemicals continues to pose difficult challenges.

SUMMARY OF THE INVENTION

The present invention provides novel compounds, the unexpected advantageous use thereof in enhancing, improving or modifying the fragrance of perfumes, colognes, toilet waters, fabric care products, personal products and the like.

One embodiment of the invention relates to novel cyclopentanols represented by Formula I set forth below:

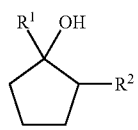

Formula I wherein $R^1$ represents a $C_1$-$C_2$ hydrocarbon group; and
wherein $R^2$ represents a $C_2$-$C_9$ hydrocarbon group.

Another embodiment of the invention relates to novel cyclopentanols represented by Formula II set forth below:

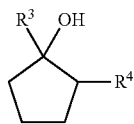

Formula II wherein $R^3$ represents a $C_1$-$C_2$ hydrocarbon group; and
wherein $R^4$ represents a $C_3$-$C_6$ hydrocarbon group.

Another embodiment of the invention relates to novel cyclopentanols represented by Formula III set forth below:

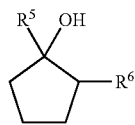

Formula III wherein $R^5$ is selected from the group consisting of ethyl and vinyl; and
wherein $R^6$ represents a $C_3$-$C_6$ hydrocarbon group.

Another embodiment of the present invention relates to a method of improving, enhancing or modifying a fragrance formulation through the addition of an olfactory acceptable amount of the novel compounds provided above.

Another embodiment of the present invention relates to a fragrance composition comprising the novel compounds provided above.

Another embodiment of the present invention relates to a fragrance product comprising the compounds provided above.

These and other embodiments of the present invention will be apparent by reading the following specification.

DETAILED DESCRIPTION OF THE INVENTION

The novel cyclopentanols represented by Formulas I-III of the present invention are illustrated, for example, by following examples.

| No. | Chemical Name |
|---|---|
| Structure 1 | 1-Ethyl-2-propyl-cyclopentanol |
| Structure 2 | 1-Ethyl-2-isopropyl-cyclopentanol |
| Structure 3 | 2-Butyl-1-ethyl-cyclopentanol |
| Structure 4 | 1-Ethyl-2-isobutyl-cyclopentanol |
| Structure 5 | 2-sec-Butyl-1-ethyl-cyclopentanol |
| Structure 6 | 1-Ethyl-2-pentyl-cyclopentanol |
| Structure 7 | 1-Ethyl-2-(3-methyl-butyl)-cyclopentanol |
| Structure 8 | 1-Ethyl-2-(2-methyl-butyl)-cyclopentanol |
| Structure 9 | 1-Ethyl-2-(1-methyl-butyl)-cyclopentanol |
| Structure 10 | 2-(1,2-Dimethyl-propyl)-1-ethyl-cyclopentanol |
| Structure 11 | 2-(2,2-Dimethyl-propyl)-1-ethyl-cyclopentanol |
| Structure 12 | 2-Ethyl-bicyclopentyl-2-ol |
| Structure 13 | 1-Ethyl-2-hexyl-cyclopentanol |
| Structure 14 | 1-Ethyl-2-(4-methyl-pentyl)-cyclopentanol |
| Structure 15 | 1-Ethyl-2-(3-methyl-pentyl)-cyclopentanol |
| Structure 16 | 1-Ethyl-2-(2-methyl-pentyl)-cyclopentanol |
| Structure 17 | 1-Ethyl-2-(1-methyl-pentyl)-cyclopentanol |
| Structure 18 | 2-(2,3-Dimethyl-butyl)-1-ethyl-cyclopentanol |
| Structure 19 | 2-(1,3-Dimethyl-butyl)-1-ethyl-cyclopentanol |
| Structure 20 | 2-(1,2-Dimethyl-butyl)-1-ethyl-cyclopentanol |
| Structure 21 | 1-Ethyl-2-(2-ethyl-butyl)-cyclopentanol |
| Structure 22 | 1-Ethyl-2-(1-ethyl-butyl)-cyclopentanol |
| Structure 23 | 1-Ethyl-2-(1-ethyl-2-methyl-propyl)-cyclopentanol |
| Structure 24 | 2-(3,3-Dimethyl-butyl)-1-ethyl-cyclopentanol |

-continued

| No. | Chemical Name |
|---|---|
| Structure 25 | 2-(2,2-Dimethyl-butyl)-1-ethyl-cyclopentanol |
| Structure 26 | 2-Cyclohexyl-1-ethyl-cyclopentanol |
| Structure 27 | 2-Cyclopentylmethyl-1-ethyl-cyclopentanol |
| Structure 28 | 1-Ethyl-2-heptyl-cyclopentanol |
| Structure 29 | 2-(3,4-Dimethyl-pentyl)-1-ethyl-cyclopentanol |
| Structure 30 | 2-Propyl-1-vinyl-cyclopentanol |
| Structure 31 | 2-Isopropyl-1-vinyl-cyclopentanol |
| Structure 32 | 2-Butyl-1-vinyl-cyclopentanol |
| Structure 33 | 2-Isobutyl-1-vinyl-cyclopentanol |
| Structure 34 | 2-sec-Butyl-1-vinyl-cyclopentanol |
| Structure 35 | 2-Pentyl-1-vinyl-cyclopentanol |
| Structure 36 | 2-(3-Methyl-butyl)-1-vinyl-cyclopentanol |
| Structure 37 | 2-(2-Methyl-butyl)-1-vinyl-cyclopentanol |
| Structure 38 | 2-(1-Methyl-butyl)-1-vinyl-cyclopentanol |
| Structure 39 | 2-(1,2-Dimethyl-propyl)-1-vinyl-cyclopentanol |
| Structure 40 | 2-(2,2-Dimethyl-propyl)-1-vinyl-cyclopentanol |
| Structure 41 | 2-Vinyl-bicyclopentyl-2-ol |
| Structure 42 | 2-Hexyl-l-vinyl-cyclopentanol |
| Structure 43 | 2-(4-Methyl-pentyl)-1-vinyl-cyclopentanol |
| Structure 44 | 2-(3-Methyl-pentyl)-1-vinyl-cyclopentanol |
| Structure 45 | 2-(2-Methyl-pentyl)-1-vinyl-cyclopentanol |
| Structure 46 | 2-(1-Methyl-pentyl)-1-vinyl-cyclopentanol |
| Structure 47 | 2-(2,3-Dimethyl-butyl)-1-vinyl-cyclopentanol |
| Structure 48 | 2-(1,3-Dimethyl-butyl)-1-vinyl-cyclopentanol |
| Structure 49 | 2-(1,2-Dimethyl-butyl)-1-vinyl-cyclopentanol |
| Structure 50 | 2-(2-Ethyl-butyl)-1-vinyl-cyclopentanol |
| Structure 51 | 2-(1-Ethyl-butyl)-1-vinyl-cyclopentanol |
| Structure 52 | 2-(1-Ethyl-2-methyl-propyl)-1-vinyl-cyclopentanol |
| Structure 53 | 2-(3,3-Dimethyl-butyl)-1-vinyl-cyclopentanol |
| Structure 54 | 2-(2,2-Dimethyl-butyl)-1-vinyl-cyclopentanol |
| Structure 55 | 2-Cyclopentanol-1-vinyl-cyclopentanol |
| Structure 56 | 2-Cyclopentylmethyl-1-vinyl-cyclopentanol |
| Structure 57 | 1-Methyl-2-propyl-cyclopentanol |
| Structure 58 | 2-Isopropyl-1-methyl-cyclopentanol |
| Structure 59 | 2-Butyl-1-methyl-cyclopentanol |
| Structure 60 | 2-Isobutyl-1-methyl-cyclopentanol |
| Structure 61 | 2-sec-Butyl-1-methyl-cyclopentanol |
| Structure 62 | 1-Methyl-2-(2-methyl-allyl)-cyclopentanol |
| Structure 63 | 1-Methyl-2-pentyl-cyclopentanol |
| Structure 64 | 1-Methyl-2-(3-methyl-butyl)-cyclopentanol |
| Structure 65 | 1-Methyl-2-(2-methyl-butyl)-cyclopentanol |
| Structure 66 | 1-Methyl-2-(1-methyl-butyl)-cyclopentanol |
| Structure 67 | 2-(1,2-Dimethyl-propyl)-1-methyl-cyclopentanol |
| Structure 68 | 2-(2,2-Dimethyl-propyl)-1-methyl-cyclopentanol |
| Structure 69 | 2-Methyl-bicyclopentyl-2-ol |
| Structure 70 | 2-Hexyl-1-methyl-cyclopentanol |
| Structure 71 | 1-Methyl-2-(4-methyl-pentyl)-cyclopentanol |
| Structure 72 | 1-Methyl-2-(3-methyl-pentyl)-cyclopentanol |
| Structure 73 | 1-Methyl-2-(2-methyl-pentyl)-cyclopentanol |
| Structure 74 | 1-Methyl-2-(1-methyl-pentyl)-cyclopentanol |
| Structure 75 | 2-(2,3-Dimethyl-butyl)-1-methyl-cyclopentanol |
| Structure 76 | 2-(1,3-Dimethyl-butyl)-1-methyl-cyclopentanol |
| Structure 77 | 2-(1,2-Dimethyl-butyl)-1-methyl-cyclopentanol |
| Structure 78 | 2-(2-Ethyl-butyl)-1-methyl-cyclopentanol |
| Structure 79 | 2-(1-Ethyl-butyl)-1-methyl-cyclopentanol |
| Structure 80 | 2-(1-Ethyl-2-methyl-propyl)-1-methyl-cyclopentanol |
| Structure 81 | 2-(3,3-Dimethyl-butyl)-1-methyl-cyclopentanol |
| Structure 82 | 2-(2,2-Dimethyl-butyl)-1-methyl-cyclopentanol |
| Structure 83 | 2-Cyclohexyl-l-methyl-cyclopentanol |
| Structure 84 | 2-Cyclopentylmethyl-l-methyl-cyclopentanol |
| Structure 85 | 2-Heptyl-1-methyl-cyclopentanol |
| Structure 86 | 2-(3,4-Dimethyl-pentyl)-1-methyl-cyclopentanol |
| Structure 87 | 2-Benzyl-1-methyl-cyclopentanol |
| Structure 88 | 1-Methyl-2-(3,5,5-trimethyl-hexyl)-cyclopentanol |

The compounds of the present invention can be prepared from cyclopentanone. The reaction steps can be depicted by a scheme shown as follows:

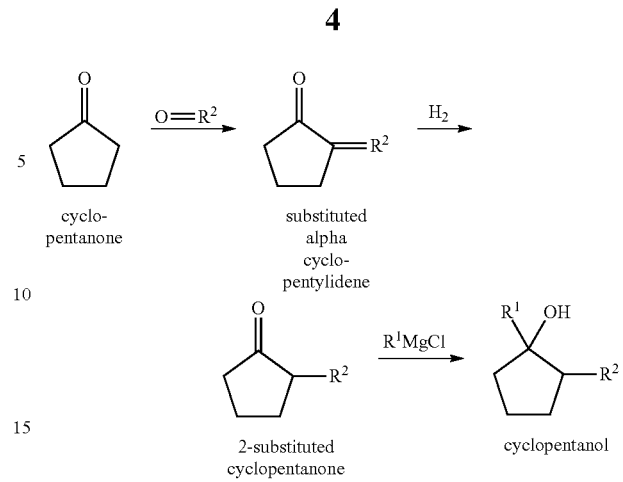

wherein $R^1$ and $R^2$ are defined as above.

The above preparation is detailed in the Examples. Materials were purchased from Aldrich Chemical Company unless noted otherwise.

The compounds of the present invention are surprisingly found to possess powerful and complex fragrance effect such as, for example, fresh, citrusy and green notes with additional woodiness and camphoraceous and earthy undertones.

The use of the compounds of the present invention is widely applicable in current perfumery products, including the preparations of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, *gardenia*, hawthorn, heliotrope, honeysuckle, hyacinth, jasmine, lilac, lily, *magnolia, mimosa, narcissus*, freshly-cut hay, orange blossom, orchid, *reseda*, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl)pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff) and (3Z)-1-[(2-methyl-2-propenyl)oxy]-3-hexene (Vivaldie).

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention may comprise a compound of the present invention and further a complementary fragrance compound as defined above.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.05 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, mol is understood to be mole, psi is understood to be pounds per square inch and mmHg be millimeters (mm) of mercury (Hg). IFF as used in the examples is understood to mean International Flavors & Fragrances Inc., New York, N.Y., USA.

Example I

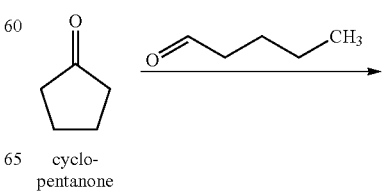

cyclo-
pentanone

-continued

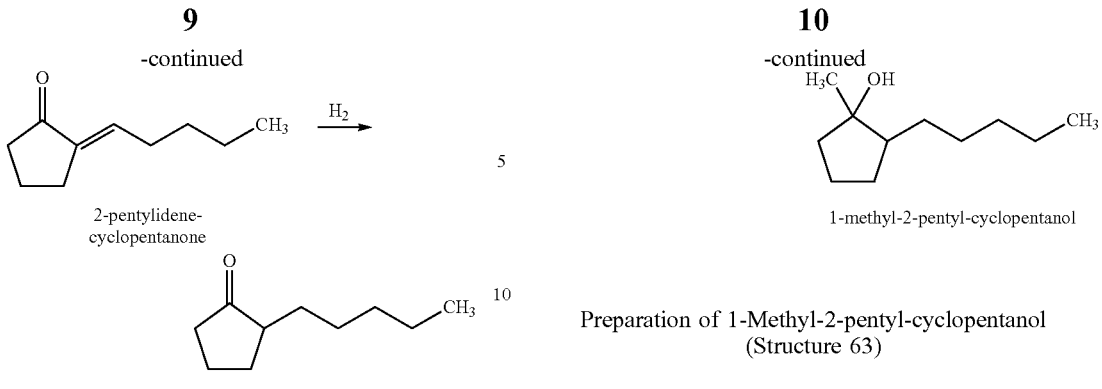

2-pentylidene-
cyclopentanone 2-pentyl-
cyclopentanone

Preparation of 2-Pentyl-cyclopentanone

A 3-L reaction flask was charged with cyclopentanone (500 g, 6 mol), water ($H_2O$) (500 mL) and sodium hydroxide (NaOH) (10 g, 0.25 mol). Valeraldehyde (430 g, 5 mol) was fed into the reaction flask over 3 hours while the temperature was maintained at 25-30° C. After the feeding was completed, the reaction was aged for 2 hours and neutralized with hydrochloric acid (HCl) (30 g, 0.3 mol) while the temperature was maintained at 25-30° C. The reaction mass was further aged for 2 hours. The organic layer was separated and washed with saturated aqueous sodium bicarbonate ($NaHCO_3$) (200 mL). The obtained crude product was fractionated to provide 2-pentylidene-cyclopentanone (523 g) having a boiling point of 122° C. at 3 mmHg. A 1-L zipper autoclave was charged with 2-pentylidine cyclopentanone (523 g) and palladium on carbon (Pd/C) (2 g). The autoclave was purged three times with nitrogen followed by three times with hydrogen. The autoclave agitator was then turned on to 1500 rpm and the pressure was set to 100 psi. The reaction was allowed to exotherm to about 120° C. and maintained at this temperature for 2 hours. The autoclave was cooled to an ambient temperature. The hydrogen was then vented and the autoclave was subsequently purged three times with nitrogen. The Pd/C was removed by filtration through Celite®. The crude product 2-pentyl-cyclopentanone (520 g) was obtained and used in following steps without further purification.

2-Pentylidene-cyclopentanone:
$^1$H NMR (500 MHz, $CDCl_3$): 6.40 ppm (t, 1H), 3.75-3.15 ppm (m, 2H), 2.70-2.55 ppm (m, 2H), 2.25-2.15 ppm (m, 1H), 1.96-2.14 ppm (m, 1H), 1.71-1.82 ppm (m, 2H), 1.48-1.57 ppm (m, 1H), 1.20-1.37 ppm (m, 3H), 0.88 ppm (t, 3H, J=6.95 Hz)

2-Pentyl-cyclopentanone:
$^1$H NMR (500 MHz, $CDCl_3$): 2.25-2.32 ppm (m, 1H), 2.18-2.25 ppm (m, 1H), 1.96-2.14 ppm (m, 3H), 1.71-1.82 ppm (m, 2H), 1.48-1.57 ppm (m, 1H), 1.20-1.37 ppm (m, 7H), 0.88 ppm (t, 3H, J=6.95 Hz)

Example II

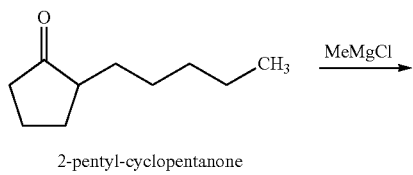

2-pentyl-cyclopentanone

-continued 1-methyl-2-pentyl-cyclopentanol

Preparation of 1-Methyl-2-pentyl-cyclopentanol (Structure 63)

A 3-L reaction flask was charged with methylmagnesium chloride (MeMgCl) solution in tetrahydrofuran (THF) (800 mL, 2.4 mol) and THF (500 mL). The reaction flask was cooled to 5-10° C. 2-Pentyl-cyclopentanone (370 g, 2.4 mol) (prepared as above in EXAMPLE I) was fed into the reaction mixture over an hour. The reaction was aged for 4 hours and then neutralized with acetic acid ($CH_3COOH$) (160 g) while the temperature was maintained at 5-10° C. The reaction mixture was poured into $H_2O$ (3 L) and toluene (1 L). The organic layer was separated and fractional distilled to afford 1-methyl-2-pentyl-cyclopentanol (245 g) having a boiling point of 150-152° C. at 3 mmHg.

$^1$H NMR (500 MHz, $CDCl_3$): 1.85-1.91 ppm (m, 1H), 1.62-1.76 ppm (m, 3H), 1.17-1.59 ppm (m, 10H), 1.27 ppm (s, 3H), 1.10-1.20 ppm (m, 2H), 0.89 ppm (t, 3H, J=6.85 Hz)

Example III

Following cyclopentanols were similarly prepared.

1-Ethyl-2-isobutyl-cyclopentanol (Structure 4) (boiling point of 145-150° C. at 5 mmHg)
$^1$H NMR (500 MHz, $CDCl_3$): 1.82-1.90 ppm (m, 1H), 1.62-1.81 ppm (m, 4H), 1.48-1.61 ppm (m, 3H), 1.34-1.47 ppm (m, 2H), 1.12-1.25 ppm (m, 2H), 1.04 ppm (s, 1H), 0.94 ppm (t, 3H, J=7.65 Hz), 0.93 ppm (d, 3H, J=6.60 Hz), 0.86 ppm (d, 3H, J=6.55 Hz)

1-Ethyl-2-pentyl-cyclopentanol (Structure 6) (boiling point of 165-166° C. at 3 mmHg)
$^1$H NMR (500 MHz, $CDCl_3$): 1.84-1.90 ppm (m, 1H), 1.60-1.78 ppm (m, 4H), 1.35-1.58 ppm (m, 6H), 1.15-1.35 ppm (m, 6H), 1.13 ppm (s, 1H), 0.94 ppm (t, 3H, J=7.5 Hz), 0.89 ppm (t, 3H, J=6.7 Hz)

1-Ethyl-2-(3-methyl-butyl)-cyclopentanol (Structure 7) (boiling point of 155-159° C. at 5 mmHg)
$^1$H NMR (500 MHz, $CDCl_3$): 1.84-1.90 ppm (m, 1H), 1.66-1.81 ppm (m, 2H), 1.64 ppm (t, 2H, J=7.45 Hz), 1.45-1.59 ppm (m, 2H), 1.35-1.45 ppm (m, 4H), 1.18-1.28 ppm (m, 1H), 1.12-1.18 ppm (m, 2H), 1.05 ppm (s, 1H), 0.94 ppm (t. 3H, J=7.50 Hz), 0.89 ppm (d, 3H, J=6.25 Hz), 0.88 ppm (d, 3H, J=6.15 Hz)

2-Ethyl-bicyclopentyl-2-ol (Structure 12) (boiling point of 135-140° C. at 5 mmHg)
$^1$H NMR (500 MHz, $CDCl_3$): 1.87-1.91 ppm (m, 1H), 1.42-1.84 ppm (m, 15H), 1.11-1.20 ppm (m, 2H), 1.10 ppm (s, 1H), 0.94 ppm (t. 3H, J=7.45 Hz)

1-Ethyl-2-heptyl-cyclopentanol (Structure 28) (boiling point of 176-178° C. at 3 mmHg)
$^1$H NMR (500 MHz, $CDCl_3$): 1.84-1.98 ppm (m, 1H), 1.61-1.78 ppm (m, 4H), 1.35-1.60 ppm (m, 6H), 1.12-1.34 ppm (m, 10H), 0.92-1.06 ppm (m, 4H), 0.88 ppm (t. 3H, J=6.53 Hz)

2-(3,4-Dimethyl-pentyl)-1-ethyl-cyclopentanol (Structure 29) (boiling point of 163-166° C. at 3 mmHg)

$^1$H NMR (500 MHz, CDCl$_3$): 1.84-1.94 ppm (m, 1H), 1.66-1.78 ppm (m, 2H), 1.62-1.66 ppm (m, 2H), 1.47-1.62 ppm (m, 3H), 1.35-1.46 ppm (m, 3H), 1.23-1.31 ppm (m, 2H), 1.11-1.22 ppm (m, 1H), 1.02-1.09 ppm (m, 2H), 0.94 ppm (t, 3H, J=7.53 Hz), 0.86 ppm (d, 3H, J=6.83 Hz, of d, J=1.53 Hz), 0.78-0.82 ppm (m, 6H)

2-Isobutyl-1-vinyl-cyclopentanol (Structure 33) (boiling point of 130-132° C. at 5 mmHg)

$^1$H NMR (500 MHz, CDCl$_3$): 5.86 ppm (d, 1H, J=17.25 Hz, of d, J=10.72 Hz), 5.26 ppm (d, 1H, J=17.27 Hz, of d, J=1.42 Hz), 5.10 ppm (d, 1H, J=10.72 Hz, of d, J=1.40 Hz), 1.44-1.96 ppm (m, 8H), 1.19 ppm (s, 1H), 1.09-1.18 ppm (m, 2H), 0.90 ppm (d, 3H, J=6.60 Hz), 0.84 ppm (d, 3H, J=6.56 Hz)

2-(3-Methyl-butyl)-1-vinyl-cyclopentanol (Structure 36) (boiling point of 125-128° C. at 3 mmHg)

$^1$H NMR (500 MHz, CDCl$_3$): 5.87 ppm (d, 1H, J=17.26 Hz, of d, J=10.75 Hz), 5.27 ppm (d, 1H, J=17.28 Hz, of d, J=1.23 Hz), 5.09 ppm (d, 1H, J=10.73 Hz, of d, J=1.18 Hz), 1.89-1.96 ppm (m, 1H), 1.74-1.88 ppm (m, 2H), 1.56-1.72 ppm (m, 3H), 1.44-1.54 ppm (m, 2H), 1.37-1.43 ppm (m, 1H), 1.29 ppm (s, 1H), 1.06-1.24 ppm (m, 3H), 0.87 ppm (d, 3H, J=6.45 Hz), 0.86 ppm (d, 3H, J=6.40 Hz)

2-Vinyl-bicyclopentyl-2-ol (Structure 41) (boiling point of 130° C. at 3 mmHg)

$^1$H NMR (500 MHz, CDCl$_3$): 5.95 ppm (d, 1H, J=17.23 Hz, of d, J=10.71 Hz), 5.27 ppm (d, 1H, J=17.27 Hz, of d, J=1.42 Hz), 5.02 ppm (d, 1H, J=10.72 Hz, of d, J=1.40 Hz), 1.70-1.91 ppm (m, 6H), 1.41-1.69 ppm (m, 8H), 1.39 ppm (s, 1H), 0.98-1.21 ppm (m, 2H)

2-Isobutyl-1-methyl-cyclopentanol (Structure 60) (boiling point of 125-130° C. at 5 mmHg)

$^1$H NMR (500 MHz, CDCl$_3$): 1.83-1.90 ppm (m, 1H), 1.49-1.80 ppm (m, 6H), 1.35-1.43 ppm (m, 1H), 1.26 ppm (s, 3H), 1.18-1.24 ppm (m, 2H), 1.14 ppm (s, 1H), 0.93 ppm (d, 3H, J=6.65 Hz), 0.86 ppm (d, 3H, J=6.55 Hz)

1-Methyl-2-(2-methyl-allyl)-cyclopentanol (Structure 62) (boiling point of 122-125° C. at 25 mmHg)

$^1$H NMR (500 MHz, CDCl$_3$): 4.72 ppm (s, 2H), 2.24 ppm (d, 1H, J=13.86 Hz, of d, J=4.10 Hz), 1.95 ppm (d, 1H, J=13.76 Hz, of d, J=10.15 Hz), 1.75-1.86 ppm (m, 1H), 1.67-1.74 ppm (m, 7H), 1.52-1.62 ppm (m, 1H), 1.40-1.46 ppm (m, 1H), 1.30 ppm (s, 3H), 1.13 ppm (s. 1H)

1-Methyl-2-(3-methyl-butyl)-cyclopentanol (Structure 64) (boiling point of 145-149° C. at 5 mmHg)

$^1$H NMR (500 MHz, CDCl$_3$): 1.84-1.91 ppm (m, 1H), 1.62-1.79 ppm (m, 3H), 1.44-1.61 ppm (m, 3H), 1.32-1.43 ppm (m, 2H), 1.27 ppm (s, 3H), 1.11-1.25 ppm (m, 4H), 0.90 ppm (d. 3H, J=6.45 Hz), 0.88 ppm (d, 3H, J=6.35 Hz)

2-Methyl-bicyclopentyl-2-ol (Structure 69) (boiling point of 125-128° C. at 5 mmHg)

$^1$H NMR (500 MHz, CDCl$_3$): 1.90-1.96 ppm (m, 1H), 1.73-1.84 ppm (m, 3H), 1.67-1.72 ppm (m, 3H), 1.42-1.67 ppm (m, 6H), 1.37-1.41 ppm (m, 1H), 1.34 ppm (s, 3H), 1.30 ppm (s, 1H), 1.10-1.21 ppm (m, 2H)

1-Methyl-2-(2-methyl-pentyl)-cyclopentanol (Structure 73) (boiling point of 105-107° C. at 3 mmHg)

$^1$H NMR (500 MHz, CDCl$_3$): 1.00-2.35 ppm (m, 15H), 1.25 ppm (s, 3H), 0.89 ppm (t, 3H, J=6.75 Hz), 0.84 ppm (d, 3H, J=6.60 Hz)

2-Heptyl-1-methyl-cyclopentanol (Structure 85) (boiling point of 175-178° C. at 3 mmHg)

$^1$H NMR (500 MHz, CDCl$_3$): 1.84-2.32 ppm (m, 2H), 1.61-1.82 ppm (m, 3H), 1.13-1.58 ppm (m, 18H), 0.88 ppm (t, 3H, J=6.60 Hz)

2-(3,4-Dimethyl-pentyl)-1-methyl-cyclopentanol (Structure 86) (boiling point of 155-158° C. at 5 mmHg)

$^1$H NMR (500 MHz, CDCl$_3$): 1.84-2.26 ppm (m, 2H), 1.48-1.81 ppm (m, 6H), 1.38-1.47 ppm (m, 2H), 1.37 ppm (s, 1H), 1.27 ppm (d, 3H, J=1.48 Hz), 1.15-1.35 ppm (m, 1H), 1.14 ppm (s, 1H), 0.96-1.12 ppm (m, 1H), 0.86 ppm (d, 3H, J=6.84 Hz), 0.81 ppm (d, 3H, J=6.68 Hz), 0.79 ppm (d, 3H, J=6.80 Hz)

2-Benzyl-1-methyl-cyclopentanol (Structure 87) (boiling point of 125-130° C. at 5 mmHg)

$^1$H NMR (500 MHz, CDCl$_3$): 7.15-7.30 ppm (m, 5H), 2.86-2.92 ppm (d, 1H, J=13.36 Hz, of d, J=4.07 Hz), 2.45-2.52 ppm (d, 1H, J=13.32 Hz, of d, J=10.41 Hz), 1.93-2.45 ppm (m, 1H), 1.61-1.85 ppm (m, 4H), 1.48-1.53 ppm (m, 2H), 1.32 ppm (s, 3H), 1.13 ppm (s, 1H)

1-Methyl-2-(3,5,5-trimethyl-hexyl)-cyclopentanol (Structure 88) (boiling point of 160-162° C. at 5 mmHg)

$^1$H NMR (500 MHz, CDCl$_3$): 1.81-2.17 ppm (m, 2H), 1.63-1.78 ppm (m, 3H), 1.34-1.55 ppm (m, 5H), 1.27 ppm (2s, 3H), 1.10-1.26 ppm (m, 3H), 0.99-1.10 ppm (m, 2H), 0.88-0.95 ppm (m, 12H)

Example IV

The fragrance properties of the above cyclopentanols were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Chemical Name | Structure | Odor Profile | Strength | Complexity |
| --- | --- | --- | --- | --- |
| 1-Ethyl-2-isobutyl-cyclopentanol (Structure 4) | 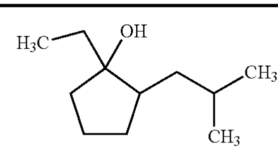 | Green note with woody background and camphoraceous and earthy undertones | 6 | 7 |
| 1-Ethyl-2-pentyl-cyclopentanol (Structure 6) | 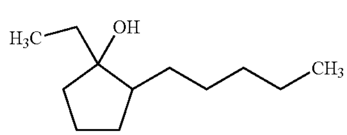 | Lactonic, sweet and creamy notes with coconut-like fruitiness and soft floral and green background | 8 | 7 |

-continued

| Chemical Name | Structure | Odor Profile | Strength | Complexity |
|---|---|---|---|---|
| 1-Ethyl-2-(3-methyl-butyl)-cyclopentanol (Structure 7) | 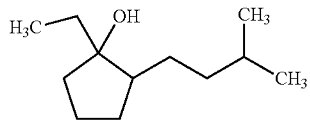 | High strength with extreme complexity; fresh, citrusy and green notes with camphoraceous and earthy undertones; additional woodiness supported by floral and fruity characters | 8 | 9 |
| 2-Ethyl-bicyclopentyl-2-ol (Structure 12) | 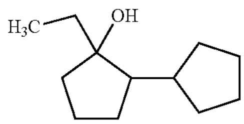 | Woodiness with solventy and chemical quality; camphoraceous, earthy and piney but fatty notes | 7 | 4 |
| 1-Ethyl-2-heptyl-cyclopentanol (Structure 28) | 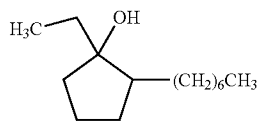 | Fruity, peachy, lactonic, floral and sweet notes; low strength and low complexity | 1 | 1 |
| 2-(3,4-Dimethyl-pentyl)-1-ethyl-cyclopentanol (Structure 29) | 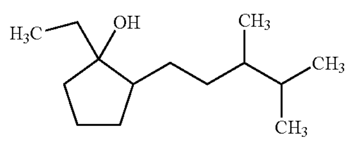 | Fruity, peachy, lactonic, floral and sweet notes; low strength and low complexity | 1 | 1 |
| 2-Isobutyl-1-vinyl-cyclopentanol (Structure 33) | 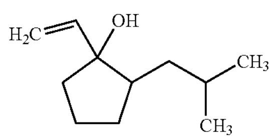 | Fresh, camphoraceous, woody and earthy notes with fatty and chemical quality and fishy, marine and oily characters | 4 | 5 |
| 2-(3-Methyl-butyl)-1-vinyl-cyclopentanol (Structure 36) | 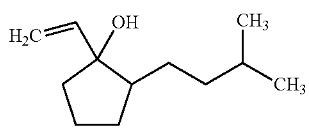 | Fresh and floral notes with fatty and dirty quality | 4 | 4 |
| 2-Vinyl-bicyclopentyl-2-ol (Structure 41) | 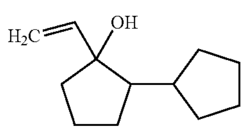 | Fresh, citrusy, woody, earthy and camphoraceous notes with chemical kerosene-like, and balsamic quality | 4 | 5 |
| 2-Isobutyl-1-methyl-cyclopentanol (Structure 60) | 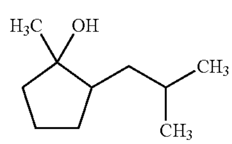 | Fresh, citrusy, floral, earthy and camphoraceous notes with green quality | 7 | 7 |
| 1-Methyl-2-(2-methyl-allyl)-cyclopentanol (Structure 62) | 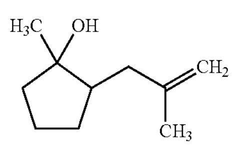 | Fresh and pine-like notes with balsamic quality | 4 | 5 |
| 1-Methyl-2-pentyl-cyclopentanol (Structure 63) | 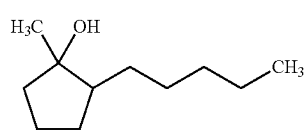 | Lactonic, fruity, floral and coconut-like notes with fatty quality | 8 | 8 |
| 1-Methyl-2-(3-methyl-butyl)-cyclopentanol (Structure 64) | 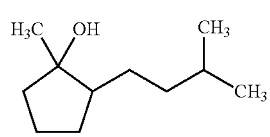 | Floral, herbaceous and piney notes but with no camphoraceous or earthy characters | 8 | 8 |

| Chemical Name | Structure | Odor Profile | Strength | Complexity |
| --- | --- | --- | --- | --- |
| 2-Methyl-bicyclopentyl-2-ol (Structure 69) | 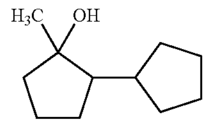 | Fresh, citrusy, herbaceous and anisic notes with balsamic and chemical quality | 6 | 5 |
| 1-Methyl-2-(2-methyl-pentyl)-cyclopentanol (Structure 73) | 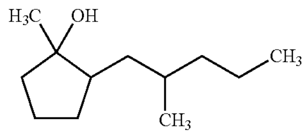 | Fresh, fruity, floral and green notes | 6 | 8 |
| 2-Heptyl-1-methyl-cyclopentanol (Structure 85) | 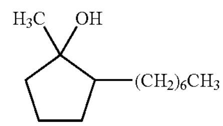 | Aldehydic note with fruity character | 7 | 6 |
| 2-(3,4-Dimethyl-pentyl)-1-methyl-cyclopentanol (Structure 86) | 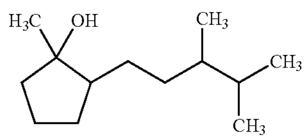 | Lactonic but slightly burnt, floral and aldehydic notes with fatty, solventy and chemical quality | 5 | 4 |
| 2-Benzyl-1-methyl-cyclopentanol (Structure 87) | 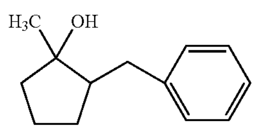 | Green note with solventy character, low strength and low complexity | 1 | 1 |
| 1-Methyl-2-(3,5,5-trimethyl-hexyl)-cyclopentanol (Structure 88) | 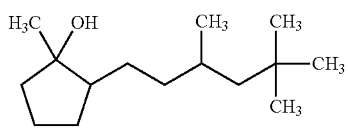 [SMILES: CC(CCC1CCCC1(C)O)CC(C)(C)C] | Floral note with rubbery and aldehydic quality | 3 | 3 |

Among all structures evaluated, Structures 6, 7, 63 and 64 exhibited particularly desirable, strong and complex odors. Their advantageous properties are unexpected.

Example V

In addition, a number of cyclopentanol analogs were prepared via hydrogenation of corresponding substituted alpha cyclopentylidines or 2-substituted cyclopentanones from the scheme described above (See, page 7).
2-Isobutyl-cyclopentanol (Structure 89)
$^1$H NMR (500 MHz, CDCl$_3$): 3.75-4.14 ppm (m, 1H), 0.82-1.84 ppm (m, 17H)
2-Pentyl-cyclopentanol (Structure 90)
$^1$H NMR (500 MHz, CDCl$_3$): 3.75-4.14 ppm (m, 1H), 1.35-1.80 ppm (m, 16H), 0.89 ppm (t, 3H, J=6.79 Hz)
Bicyclopentyl-2-ol (Structure 91)
$^1$H NMR (500 MHz, CDCl$_3$): 3.75-4.14 ppm (m, 1H), 2.05-2.20 (m, 2H), 1.45-1.75 ppm (m, 15H)
2-Heptyl-cyclopentanol (Structure 92)
$^1$H NMR (500 MHz, CDCl$_3$): 3.75-4.14 ppm (m, 1H), 1.10-1.80 ppm (m, 20H), 0.87 ppm (t, 3H, J=6.79 Hz)
2-Benzyl-cyclopentanol (Structure 93)
$^1$H NMR (500 MHz, CDCl$_3$): 7.00-7.25 ppm (m, 5H), 3.75-4.14 ppm (m, 1H), 2.10-2.60 ppm (m, 3H), 1.50-1.80 ppm (m, 7H)
2-Octyl-cyclopentanol (Structure 94)
$^1$H NMR (500 MHz, CDCl$_3$): 3.75-4.14 ppm (m, 1H), 1.10-1.80 ppm (m, 22H), 0.87 ppm (t, 3H, J=6.79 Hz)
2-(1-Vinyl-hex-5-enyl)-cyclopentanol (Structure 95)
$^1$H NMR (500 MHz, CDCl$_3$): 5.60-5.79 ppm (m, 2H), 4.80-5.05 ppm (m, 4H), 3.75-4.14 ppm (m, 1H), 1.35-2.20 ppm (m, 15H)
2-(5,6-Dimethyl-cyclohex-3-enyl)-cyclopentanol (Structure 96)
$^1$H NMR (500 MHz, CDCl$_3$): 5.35-5.60 ppm (m, 2H), 3.75-4.14 ppm (m, 1H), 1.45-2.25 ppm (m, 13H), 0.80-0.95 ppm (m, 6H)
2-(2-Phenyl-propyl)-cyclopentanol (Structure 97)
$^1$H NMR (500 MHz, CDCl$_3$): 7.05-7.25 ppm (m, 5H), 3.75-4.14 ppm (m, 1H), 2.80-3.10 ppm (m, 1H), 1.50-2.00 ppm (m, 10H), 1.29 ppm (d, 3H, J=6.75 Hz)
2-((E)-3,7-Dimethyl-octa-2,6-dienyl)-cyclopentanol (Structure 98)
$^1$H NMR (500 MHz, CDCl$_3$): 5.15-5.25 ppm (m, 2H), 3.75-4.14 ppm (m, 1H), 1.20-2.25 ppm (m, 23H)
2-(1,5-Dimethyl-1-vinyl-hex-4-enyl)-cyclopentanol (Structure 99)
$^1$H NMR (500 MHz, CDCl$_3$): 5.70-5.80 ppm (m, 1H), 4.90-5.15 ppm (m, 3H), 3.75-4.14 ppm (m, 1H), 1.25-1.90 ppm (m, 18H), 1.04 ppm (s, 3H)
2-[2-(2,2,3-Trimethyl-cyclopentyl)-ethyl]-cyclopentanol (Structure 100)
$^1$H NMR (500 MHz, CDCl$_3$): 3.75-4.14 ppm (m, 1H), 1.61-1.84 ppm (m, 6H), 1.31-1.59 ppm (m, 7H), 1.02-1.24 ppm (m, 5H), 0.72-0.92 ppm (m, 6H), 0.50 ppm (s, 3H)
2-(2,2,6-Trimethyl-cyclohexylmethyl)-cyclopentanol (Structure 101)

¹H NMR (500 MHz, CDCl₃): 3.77-4.14 ppm (m, 1H), 0.98-2.01 ppm (m, 18H), 0.74-0.98 ppm (m, 9H)

2-(4-Isopropyl-benzyl)-cyclopentanol (Structure 102)

¹H NMR (500 MHz, CDCl₃): 7.09-7.20 ppm (m, 4H), 3.77-4.14 ppm (m, 1H), 2.48-2.88 ppm (m, 3H), 1.65-2.15 ppm (m, 8H), 1.24 ppm (d, 6H, J=7.03 Hz)

2-(4-tert-Butyl-benzyl)-cyclopentanol (Structure 103)

¹H NMR (500 MHz, CDCl₃): 7.27-7.37 ppm (m, 2H), 7.12-7.17 ppm (m, 2H), 3.77-4.14 ppm (m, 1H), 2.48-2.86 (m, 2H), 1.20-2.08 ppm (m, 8H), 1.31 ppm (s, 9H)

1-Cyclopropyl-2-pentyl-cyclopentanol (Structure 104)

¹H NMR (500 MHz, CDCl₃): 1.08-2.03 (m, 15H), 1.02 (br. S., 1H), 0.77-0.97 (m, 4H), 0.28-0.50 (m, 3H), 0.17-0.27 (m, 1H)

Example VI

The fragrance properties of the above cyclopentanol analogs (i.e., Structures 89-104) were also evaluated. Odor profiles are reported in the following:

| Chemical Name | Structure | Odor Profile |
| --- | --- | --- |
| 2-Isobutyl-cyclopentanol (Structure 89) | 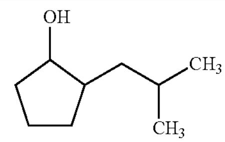 | No unique odor note, no complexity |
| 2-Pentyl-cyclopentanol (Structure 90) | 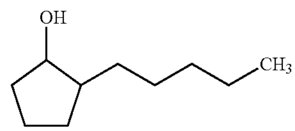 | Green note with rough character, no strength or complexity |
| Bicyclopentyl-2-ol (Structure 91) | 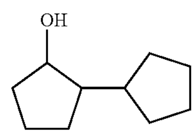 [SMILES: OC1CCCC1C1CCCC1] | Naphthalene-like, chemical and sweaty notes |
| 2-Heptyl-cyclopentanol (Structure 92) | 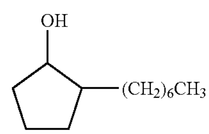 | Fatty note, no complexity |
| 2-Benzyl-cyclopentanol (Structure 93) | 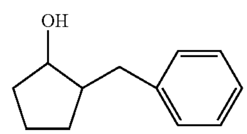 [SMILES: OC1CCCC1Cc1ccccc1] | Dirty carbinol, acidic and sweaty notes |
| 2-Octyl-cyclopentanol (Structure 94) | 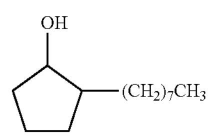 | Green note with skunky character, no strength or complexity |
| 2-(1-Vinyl-hex-5-enyl)-cyclopentanol (Structure 95) | 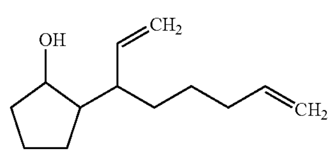 | Dirty, sulfur and mushroom-like notes |
| 2-(5,6-Dimethyl-cyclohex-3-enyl)-cyclopentanol (Structure 96) | 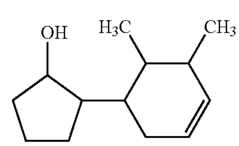 | Chemical note, no strength or complexity |
| 2-(2-Phenyl-propyl)-cyclopentanol (Structure 97) | 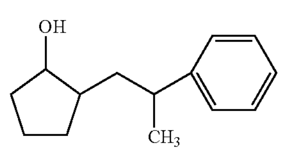 | Chessy and acidic notes |

| Chemical Name | Structure | Odor Profile |
| --- | --- | --- |
| 2-((E)-3,7-Dimethyl-octa-2,6-dienyl)-cyclopentanol (Structure 98) | 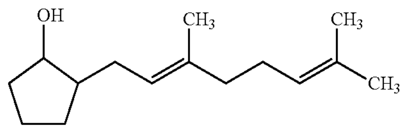 [SMILES: CC(C)=CCC/C(C)=C/CC1CCCC1O] | Very fatty note |
| 2-(1,5-Dimethyl-1-vinyl-hex-4-enyl)-cyclopentanol (Structure 99) | 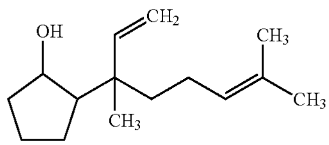 [SMILES: C=CC(C)(CCC=C(C)C)C1CCCC1O] | Very chemical note |
| 2-[2-(2,2,3-Trimethyl-cyclopentyl)-ethyl]-cyclopentanol (Structure 100) | 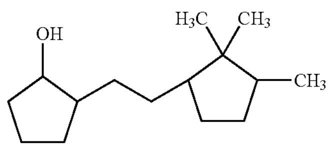 [SMILES: CC1CCC(CCC2CCCC2O)C1(C)C] | Slightly floral but very weak note |
| 2-(2,2,6-Trimethyl-cyclohexylmethyl)-cyclopentanol (Structure 101) | 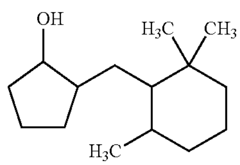 | Chemical and very weak note |
| 2-(4-Isopropyl-benzyl)-cyclopentanol (Structure 102) | 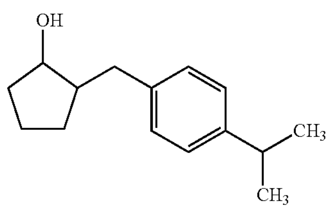 [SMILES: CC(C)c1ccc(CC2CCCC2O)cc1] | Slightly floral but very weak note |
| 2-(4-tert-Butyl-benzyl)-cyclopentanol (Structure 103) | 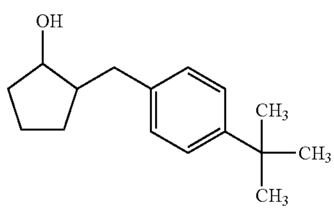 [SMILES: CC(C)(C)c1ccc(CC2CCCC2O)cc1] | Slightly woody but very weak note |
| 1-Cyclopropyl-2-pentyl-cyclopentanol (Structure 104) | 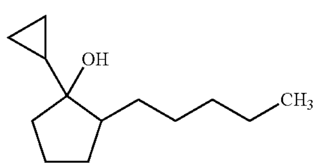 | Green note, no strength or complexity |

The evaluation of cyclopentanols and cyclopentanol analogs in the above examples has surprisingly showed that the 1-substituted cyclopentanols of EXAMPLE IV, wherein the substitution is a $C_1$-$C_2$ hydrocarbon group, possess desirable, strong and complex odors, which are not observed in the cyclopentanol analogs of EXAMPLE VI. Such advantageous properties of 1-substituted cyclopentanols are accordingly unexpected and superior.

What is claimed is:

1. A fragrance formulation containing an olfactory acceptable amount of a compound selected from the group consisting of:
   1-ethyl-2-pentyl-cyclopentanol;
   1-ethyl-2-(3-methyl-butyl)-cyclopentanol;
   1-methyl-2-pentyl-cyclopentanol; and
   1-methyl-2-(3-methyl-butyl)-cyclopentanol.

2. The fragrance formulation of claim 1, wherein the olfactory acceptable amount is from about 0.005 to about 50 weight percent of the fragrance formulation.

3. The fragrance formulation of claim 1, wherein the olfactory acceptable amount is from about 0.5 to about 25 weight percent of the fragrance formulation.

4. The fragrance formulation of claim 1, wherein the olfactory acceptable amount is from about 1 to about 10 weight percent of the fragrance formulation.

5. The fragrance formulation of claim 1 further comprising a material selected from the group consisting of a polymer and a non-polymer.

6. The fragrance formulation of claim 5, wherein the non-polymer is selected from the group consisting of an oligomer, a surfactant, an emulsifier, a fat, a wax, a phospholipid, an organic oil, a mineral oil, a petrolatum, a natural oil, a perfume fixative, a fiber, a starch, a sugar and a solid surface material.

7. The fragrance formulation of claim 6, wherein the solid surface material is selected from the group consisting of zeolite and silica.

* * * * *